United States Patent [19]

Schutt et al.

[11] Patent Number: 5,017,009
[45] Date of Patent: May 21, 1991

[54] SCATTERED TOTAL INTERNAL REFLECTANCE IMMUNOASSAY SYSTEM

[75] Inventors: Ernest G. Schutt, Long Valley; Richard S. Dondero, Riverdale, both of N.J.; William P. Hansen, Middleboro, Mass.; George B. Hovorka, Hyde Park, Mass.; Raymond E. Meyer, Arlington, Mass.; Karin L. Utberg, Bridgewater; David L. Greenwood, both of N.J.

[73] Assignee: Ortho Diagnostic Systems, Inc., Raritan, N.J.

[21] Appl. No.: 149,243

[22] Filed: Jan. 27, 1988

Related U.S. Application Data

[63] Continuation-in-part of Ser. No. 879,236, Jun. 26, 1986, abandoned.

[51] Int. Cl.⁵ ............................................. G01N 21/49
[52] U.S. Cl. .................................................... 358/338
[58] Field of Search ................................ 356/336, 338

[56] References Cited

U.S. PATENT DOCUMENTS

| | | |
|---|---|---|
| 3,939,350 | 2/1976 | Kronick et al. |
| 3,975,084 | 8/1976 | Block ............................... 356/338 |
| 4,181,441 | 1/1980 | Noller .............................. 356/414 |
| 4,313,734 | 2/1982 | Leuvering .......................... 23/230 |
| 4,447,546 | 5/1984 | Hirschfeld . |
| 4,456,374 | 6/1984 | Langberg . |
| 4,521,522 | 6/1985 | Lundstrom et al. ................. 436/525 |
| 4,558,014 | 12/1985 | Hirschfeld et al. . |

FOREIGN PATENT DOCUMENTS

| | | |
|---|---|---|
| 91636 | 10/1983 | European Pat. Off. . |
| 167335 | 1/1986 | European Pat. Off. . |
| 170376 | 2/1986 | European Pat. Off. . |

OTHER PUBLICATIONS

Gribnau et al., "Particle-Labelled Immunoassays: A Review", *Journal of Chromatography* 376 (1986), pp. 175-189.

Lee, E-H et al., "Angular Distribution of Fluorescence from Liquids and Monodispersed Spheres by Evanescent Wave Excitation", Applied Optics 18, No. 6:862-868 (1979).

Sutherland, R. M. et al., "Immunoassays at a Quartz-Liquid Interface: Theory, Instrumentation and Preliminary Application to the Fluorescent Immunoassay of Human Immuoglobulin G", J. Immunol. Met. 74:253-265 (1985).

Sutherland, R. M. et al., "Optical Detection of Antibody-Antigen Reactions at a Glass-Liquid Interface", Clin. Chem. 30/9:1533-1538 (1984).

Sutherland, R. M. et al., "Preliminary Results Obtained with a No-Label, Homogeneous, Optical Immunoassay for Human Immunoglobulin G", Analytical Letters, 17(B1):43-53 (1984).

Hellen, E. H. et al., "Fluorescence Emission at Dielectric and Metal-Film Interfaces", J. Opt. Soc. Am., 4/3:337-350 (1987).

*Primary Examiner*—Richard A. Rosenberger
*Attorney, Agent, or Firm*—Michael Stark; Gale F. Matthews

[57] ABSTRACT

A new immunoassay system is provided for the detection of ligands or ligand binding partners in solution in a heterogeneous format. The invention relies upon the detection of back scattered light from an evanescent wave disturbed by the presence of a colloidal gold label brought to the interface by an immunological reaction. The evanescent wave existing at the interface in turn is the result of a totally internally reflected incident light wave. Placement of the detector at a back angle above the critical angle insures a superior signal-to-noise ratio.

19 Claims, 6 Drawing Sheets

FIG-8 ature of the specificity of the fluorescent label with
SCATTERED TOTAL INTERNAL REFLECTANCE IMMUNOASSAY SYSTEM This application is a continuation-in-part of U.S. Ser. No. 879,236, filed June 26, 1986, now abandoned, the contents of which are hereby incorporated by reference into the subject application.

FIELD OF THE INVENTION

This invention relates to immunoassays generally and more particularly provides a new system for performing virtual homogeneous immunoassaYs employing colloidal gold.

BACKGROUND OF THE INVENTION

Many human disease states are identified on the basis of immunoassay techniques which rely upon the specificity between immunoglobulin, whether monoclonal or polyclonal, and their respective binding partners, which may be haptens, antigens, or other analytes, all of which may hereafter be collectively and interchangeably referred to herein as "ligands" and "ligand binding partners." Furthermore, "ligand" also means any molecule having an affinity to bind or complex with a "ligand binding partner", including chelators, immunobinders, nucleic acid strands, bioreceptors, and hydrophobic binders. Over the past fifteen or so years, there has been a substantial amount of effort involved in the development of immunoassay techniques utilizing the so-called sandwich and competitive techniques. The sandwich technique involves the immobilization of an antigen by one antibody and then subsequent labeling by attachment of a second antibody having associated therewith a detectable label. Reverse immunoassays for the detection of antibody are similar but instead put antigen on the surface for reaction with the sample antibody. Competitive techniques are useful for antigens having only a single epitopic site for reaction with an antibody. Accordingly, and as the name implies, such techniques rely upon the competition of the antigen with another labeled antigen for a binding site on an immobilized antibody. The substitutions necessary for antibody detection tests are obvious and need not be covered here in any great detail.

Of great importance in the laboratory is the development of highly sensitive techniques which can be run in either batch random access, panel, or stat modes. Preferably, such techniques will be homogeneous in nature, i.e., and as used herein, they will be conducted solely within one container without any accompanying requirement to physically separate out components following reactions during the assay.

It is one object of the present invention to provide a new immunoassay system which is highly sensitive and which is homogeneous in nature.

U.S. Pat. 3,939,350 to Kronick and the Kronick citations therein referenced describe an immunoassay system which allows for the measurement of biochemical analytes by fluorescence in a liquid sample. Kronick employs a physical phenomenon known under the name of total internal reflectance. This optical phenomenon occurs wherein light, when directed through a high refractive index material toward the interface of that material with a second material having a lower refractive index at greater than a critical angle, all light is reflected from that interface save for a microscopic evanescent wave which propagates into the second material for only a short distance. The second material may, for instance, be water or another aqueous medium in which an assay is being conducted. Kronick noted that when he brought materials which had been fluorescently labeled down to the interface and within the field of the evanescent wave, he could energize the fluorescent molecules and detect fluorescence which then emanated into the overlying solution. The Kronick system, however, looks at fluorescence which cannot be readily modified by alteration of the fluorescent labels in order to suit the system under study. Due to the nature of the specificity of the fluorescent label with respect to the wavelength of the excitation frequency, one is limited to a discrete light source providing the critical excitation frequency. To date, most investigators favor the He-Ne laser light source due to its reliability and low cost as well as the low cost of associated optics. Such a light source, however, brings concomitant difficulties in tailoring fluorescent molecules to be excited by the He-Ne laser output. The organic, inorganic, and bio-organic techniques required are especially difficult to control in the immunoassay arena. Further, Kronick's reliance on fluorescence is accompanied by additional disadvantages associated with bleaching of the fluorescent molecules and generally critical matching of fluorescent molecule excitation wavelength with laser output wavelength necessary to obtain good quantum efficiency.

It is an object of the present invention to provide a new immunoassay system which avoids the disadvantages associated with fluorescent labels and the criticality associated with matching an excitation source.

It is another object of the present invention to employ the principles of total internal reflection but with far greater flexibility regarding the choice of illumination sources. U.S. Pat. 4,181,441 to Noller describes a system similar to that of Kronick. Noller, however, taught that the assay should be conducted by measurement of light absorption in a liquid sample which could then be correlated to the presence of biochemical analytes. Although the Noller system employs different physical principles than the Kronick system, light absorption measurements are similarly subject to poorer signal-to-noise ratios due to small differences in large light signals thereby making such a system inherently less sensitive than desired. It is another object of the present invention to avoid employing light absorption measurements while still gaining the advantages to be provided by the total internal reflectance phenomenon.

U.S. Pat. No. 4,521,522 to Lundstrom teaches yet another immunoassay based upon reflectance and the use of Brewster s angle. This system relies upon a different optical phenomenon wherein directing a light beam, polarized in the plane of incidence, upon an interface, for example that formed between plastic and liquid, results in the transmission of a strong light beam into the liquid when such light strikes the interface at the Brewster angle. At the Brewster angle, substantially no light is reflected.

The Brewster angle is a function of the refractive indices of the two materials as well as the direction of polarization. Lundstrom noted that upon the growth of a biochemical layer at the interface, the Brewster angle condition would be disrupted resulting in increasing light reflectance, particularly at angles less than the Brewster angle. Unfortunately, the Lundstrom assay only works effictively with a wash step since the transmission of the beam into the liquid also results in the generation of light scatter and thus a spurious signal.

It is another object of the present invention to utilize light scatter but to avoid light scatter generated by the transmission of light into the liquid which occurs naturally when light is directed at an interface at the Brewster angle. Accordingly, it is yet another object of the present invention to avoid employing a Brewster angle condition.

SUMMARY OF THE INVENTION

In accordance with various aspects and the principles of the present invention, there is provided an immunoassay system which utilizes scattered total internal reflectance (STIR) as a measure of the presence of particular ligands to be determined in an aqueous solution. The invention relies in part upon the identification of the critical angle associated with total internal reflectance. The angle is largely a function of the refractive index of the material through which an incident light wave is directed, e.g. plastic, and the relatively lower refractive index of the material in which the immunoassay is being conducted, e.g. an aqueous solution. It is measured from a line perpendicular to the interface between the two materials, and thus at its maximum, 90°, will lie in the plane of the interface.

Light directed through the plastic toward the interface formed by the aqueous sample and plastic materials at the critical angle will result in total internal reflectance of the light within the plastic. It is recognized that no materials in the real world are perfect and accordingly, it is preferred that the incident light be directed toward the interface at an angle several degrees greater than the critical angle, most preferably in the range of approximately 6° greater in order to ensure that the basic conditions of total internal reflectance are met. At such an angle, the incident collimated light, preferably from a laser, is totally internally reflected within the plastic save for the propagation of the evanescent wave parallel to the surface of the plastic and approximately $1/4\lambda$ from the surface. Similarly, smooth surfaces at the interface are preferred for optimum signal quality. Unlike conventional fluorescent techniques including those of Kronick, the present assay system is flexible with respect to light wavelength since particle size may be readily adjusted to match the available light source (or vice versa) to provide acceptable light scatter. Fluorescent molecules are not readily adjustable with respect to excitation wavelength.

Most ideally, the light source will be a He-Ne light source, however, other lasers with different wavelength outputs have been used and still other sources suggest themselves including light emitting diodes and other nonlaser light sources.

Applicants' immunoassay system further relies upon conventional immunoassay techniques. However, applicants' immunoassay system also employs a particulate label having a higher refractive index than that of the solution, and most preferably also higher than the first light transmissive material, e.g. plastic in the foregoing example. Such Particles would include, for instance, red blood cells, other materials having a highly reflective surface such as metallic particles, and nonmetallic substances such as glass or plastics, e.g. latex particles, and the like. Most preferably, colloidal gold is used as a label for the solution phase immunologically active component. While the use of colloidal gold as a label is known, see for example U.S. Pat. No. 4,313,734 Leuvering, almost no nonagglutination related uses of the label have been made to date due to the difficulties associated with its detection, particularly in homogeneous type systems. It was surprisingly discovered by the inventors hereof that the unique combination of STIR with colloidal gold has resulted in an extremely efficient and sensitive homogeneous assay system. It is believed, but not known for certain that this is due primarily to the interaction of the colloidal gold particles with the evanescent wave. Indeed, experience implies that particles having an increasingly higher index of refraction than that of the underlying solid generally increasingly scatter light. While particles with indices of refraction less than the underlying solid, providing they are also not equal to that of the aqueous medium, would also scatter light, such are less preferred.

Assuming for the moment a conventional sandwich technique, one immunoglobulin or ligand binding partner is immobilized on the surface and binds antigen or other ligand to be determined. Thereafter, (or simultaneously, or if not previously) a second immunoglobulin, directed at a second epitopic site on the ligand, and labeled directly or indirectly with colloidal gold, binds to the ligand creating the so-called "sandwich". In this arrangement, the presence of the colloidal gold disrupts the propagation of the evanescent wave resulting in scattered light which may be detected by a photomultiplier or other light sensor to provide a responsive signal. Another important aspect of the present invention involves the physical location of the detector. The detector is ideally placed at an angle greater than the critical angle and in a location whereby only light scattered backward toward the light source is detected. This location thereby ideally avoids the detection of spurious scattered light within the bulk liquid medium.

Another feature of the instant invention is that the immunoassays are diffusion rate controlled and not particularly temperature dependent. This is in strong contrast to ELISA and various other immunoassay techniques wherein temperature control is critical since small changes in temperature in such systems results in wide variations in assay results per unit of time.

It was surprisingly found by the inventors hereof, that as a result of the combination of these elements, rapid, sensitive results could be obtained in a homogeneous environment without requiring the complicated equipment previously associated with colloidal gold assay techniques.

BRIEF DESCRIPTION OF THE DRAWINGS

The critical angle, $\theta_c$, is only defined in the higher refractive index medium and can range from 0° to 90°. Light propagating from a point on the fluid contacting surface 58 at the total internal reflectance critical angle 55 would follow the path depicted as 57. All light propagating through the optically transparent member 53 from a point on the fluid contacting surface 58 between the plane of the sample fluid contacting surface 51 and the total internal reflectance critical angle 55 of the fluid contacting surface, will propagate in the range depicted as 56.

DETAILED DESCRIPTION OF THE INVENTION AND BEST MODE

The present invention provides an apparatus for detecting the presence of an analyte of interest in a sample. This apparatus comprises a light source; housing means for receiving an optically transparent member having a sample contacting surface, said member in said housing means being disposed such that the sample contacting surface is illuminated with light emitted from said light source; and photodetection means which excludes the detection of light which propagates in a geometric optical path from the light source, said photodetection means being capable of detecting elastically-scattered light which propagates through the optically transparent member from the illuminated sample contacting surface between the plane of the sample contacting surface and the total internal reflectance critical angle of the sample contacting surface. Within this application, "photodetection means" is defined as a system for detecting photons having a wavelength equal to the wavelength of the illuminating light, and includes combinations of photon detectors (e.g. photomultiplier tubes), lenses, mirrors, light filters, optical fibers, prisms, apertures, and masks. A geometric optical path is the path that a family of light rays will follow based on first order reflection and refraction of idealized surfaces (imperfection free) and ignoring the effects of surface and bulk material imperfections, diffraction, interference, scatter, and partial reflection at surfaces. Further, within this application, "elastically-scattered light" (also referrred to herein as "scatter" and "scattered light") means incident light which has been redirected by an object without changing the wavelength of the light, by means other than dopler shifting, due to the difference in the refractive index of the object and its surrounding medium. Fluorescence, also known as inelastic scatter, is the light emitted by a light absorbing molecule after the molecule has absorbed a photon of light. The wavelength of the absorbed light is less than the wavelength of the emitted light. Flouorescent light is always of a wavelength different from the light incident on the light absorbing molecule.

"Critical angle", also referred to herein as "total internal reflectance critical angle", is the angle (less than 90°) measured from the line perpendicular to an interface between materials of different refractive indexes, beyond which total internal reflection can occur, and is defined by the equation $$\theta_c = \sin^{-1}\left(\frac{n_1}{n_2}\right)$$

wherein $n_1$ is the lower refractive index and $n_2$ is the higher refractive index of the two mediums forming the interface. The critical angle can only exist in the higher refractive index medium. Light which illuminates the interface from the lower refractive index material at any angle (0° to 90°) cannot be refracted into the higher refractive index medium at an angle greater than or equal to the critical angle. Total internal reflection occurs exclusively when an interface between materials of different refractive indexes is illuminated from the higher refractive index medium beyond the critical angel, causing all the incident illumination to be reflected at the interface unless it is perturbed by diffraction, scatter, or absorption.

The present invention also provides another apparatus for detecting the presence of an analyte of interest in a sample. This apparatus comprises a light source; housing means for receiving an optically transparent member having a sample contacting surface, said member in said housing means being disposed such that the sample contacting surface is illuminated with light emitted from said light source which propagates through the optically transparent member at angles between the plane of the sample contacting surface and the critical angle for total internal reflectance; and photodetection means which excludes the detection of light which propagates in a geometric optical path from the light source, said photodetection means being capable of detecting elastically-scattered light which propagates through the optically transparent member from the illuminated sample contacting surface between the plane of the sample contacting surface and the total internal reflectance critical angle.

Suitable light sources for the apparatuses of the present invention provide collimated or uncollimated light, polarized or unpolarized light, or monochromatic or polychromatic light. Preferred light sources include lasers (e.g., He-Ne lasers), light emitting diodes (LEDs), flash lamps, arc lamps, incandescent lamps, and fluorescent discharge lamps.

Suitable optically transparent members, e.g., cuvettes, are comprised of glass, quartz, silicon, plastics such as polycarbonate, acrylic, or polystyrene, or oils comprising silicone or high molecular weight hydrocarbons.

Suitable photodetection means comprise photon detectors such as photomultiplier tubes, photodiodes (e.g., PIN diodes and gallium-aluminum-arsenide diodes), cadmium sulfide photoresistive cells, phototubes, and pyrolytic detectors. Also provided is a method for detecting the presence of a light scattering molecule on the surface of an optically transparent material. This method comprises illuminating said light scattering molecule, detecting light scattered elastically by said light scattering molecule which propagates through said optically transparent material between the plane of the surface of the optically transparent material on which the light scattering molecule is located and the total internal reflectance critical angle of the surface on which the light scattering molecule is located, and correlating detected, elastically-scattered light to the presence of the light scattering molecule on the surface of the optically transparent material. Within this application, an "evanescent wave" means a nonpropagating light wave such as a wave in the region of a surface on the side of the surface opposite the side of illumination, produced when the illuminating light undergoes total internal reflection. Also within this application a "light scattering molecule" means a molecule which causes incident light to be elastically scattered. "Molecule" includes, in the case of crystalline and elemental materials, two or more atoms.

Still further, the present invention provides a method for detecting the presence of a light scattering molecule on the surface of an optically transparent material. This method comprises illuminating said light scattering molecule with an evanescent wave resulting from a light wave which propagates through said optically transparent material, detecting light scattered elastically by said light scattering molecule which propagates through said optically transparent material between the plane of the surface of the optically transparent material on which the light scattering molecule is located and the total internal reflectance critical angle of the surface on which the light scattering molecule is located, and correlating detected, elastically-scattered light to the presence of the light scattering molecule on the surface of the optically transparent material.

Further provided is a method for detecting an analyte in a fluid sample wherein said analyte is a ligand of a ligand - ligand binding partner pair. This method comprises the steps of:

a) providing an optically transparent material having a refractive index greater than the refractive index of said fluid sample, said optically transparent material having a sample contacting surface to which a plurality of ligand binding partners of said ligand - ligand binding partner pair are immobilized;

b) further providing light scattering particle-labeled ligands capable of forming complexes with said immobilized ligand binding partners;

c) contacting said fluid sample and said light scattering particle-labeled ligands with said sample contacting surface under conditions such that said analyte and said light scattering particle-labeled ligands each form complexes with said immobilized ligand binding partners;

d) illuminating said complexes with an evanescent wave resulting from a light wave which propagates through said optically transparent material;

e) detecting light scattered elastically by said light scattering particles of said complexes;

f) correlating elastically-scattered light to the presence of complexes on said sample contacting surface; and g) comparing the presence of complexes on the sample contacting surface with the presence of complexes on a sample contacting surface for a standard control, thereby detecting the analyte in the fluid sample.

Within this application, "particle" means one or more molecules. "Labeled" means directly linked, e.g., conjugated, cross-linked, or adsorbed, or indirectly linked, e.g., linked via an antibody.

Further yet is provided a method for detecting an analyte in a fluid sample wherein said analyte is a ligand of a ligand - ligand binding partner pair. This method comprises the steps of:

a) providing an optically transparent material having a refractive index greater than the refractive index of said fluid sample, said optically transparent material having a sample contacting surface to which a plurality of ligand binding partners of said ligand - ligand binding partner pair are immobilized;

b) further providing light scattering ligands caPable of forming complexes with said immobilized ligand binding partners;

c) contacting said fluid sample and said light scattering ligands with said sample contacting surface under conditions such that said analyte and said light scattering ligands each form complexes with said immobilized ligand binding partners;

d) illuminating said complexes;

e) detecting light scattered elastically by light scattering ligands of said complexes and which propagates through said optically transparent material from the sample contacting surface between the plane of the sample contacting surface and the total internal reflectance critical angle of the sample contacting surface;

f) correlating elastically-scattered light to the presence of complexes on said sample contacting surface; and g) comparing the presence of complexes on the sample contacting surface with the presence of complexes on a sample contacting surface for a standard control, thereby detecting the analyte in the fluid sample.

Within this application, "light scattering ligands" means ligands or light scattering particle-labeled ligands which cause incident light to be elastically scattered.

Further still is provided a method for detecting an analyte in a fluid sample wherein said analyte is a ligand of a ligand - ligand binding partner pair. This method comprises a) providing an optically transparent material having a refractive index greater than the refractive index of said fluid sample, said optically transparent material having a sample contacting surface to which a plurality of ligand binding partners of said ligand - ligand binding partner pair are immobilized;

b) further providing light scattering ligands capable of forming complexes with said immobilized ligand binding partners;

c) contacting said fluid sample and said light scattering ligands with said sample contacting surface under conditions such that said analyte and said light scattering ligands each form complexes with said immobilized ligand binding partners;

d) illuminating said complexes with an evanescent wave resulting from a light wave which propagates through said optically transparent material;

e) detecting light scattered elastically by light scattering ligands of said complexes and which propagates through said optically transparent material from the sample contacting surface between the plane of the sample contacting surface and the total internal reflectance critical angle of the sample contacting surface;

f) correlating elastically-scattered light to the presence of complexes on said sample contacting surface; and g) comparing the presence of complexes on the sample contacting surface with the presence of complexes on a sample contacting surface for a standard control, thereby detecting the analyte in the fluid sample.

In one embodiment of the invention, the methods provided herein may be performed wherein the sample contacting surface is contacted with the fluid sample before being contacted with the ligands<In another embodiment of the invention, the sample contacting surface is contacted with the ligands before being contacted with the fluid sample. In yet a further embodiment of the invention, the sample contacting surface is simultaneously contacted with said fluid sample and the ligands. In still another embodiment of the invention, the sample is mixed with the ligands so as to form a mixture, and the mixture is contacted with the sample contacting surface.

Furthermore, in a preferred embodiment of the invention, light scattering particle-labeled ligands comprise ligands labeled with colloidal gold particles.

In still another embodiment of the invention, a method is provided for detecting an analyte in a fluid sample. In this method the analyte is a ligand having an epitope for which a first ligand binding partner is specific and an epitope for which a second ligand binding partner is specific. The method comprises:

a) providing an optically transparent material having a refractive index greater than the refractive index of said fluid sample, said optically transparent material having a sample contacting surface to which a plurality of first ligand binding partners are immobilized;

b) further providing light scattering particle-labeled second ligand binding partners;

c) contacting said fluid sample and said light scattering particle-labeled second ligand binding partners with said sample contacting surface under conditions such that immobilized first ligand binding partner : analyte : light scattering particle-labeled second ligand binding partner complexes are formed;

d) illuminating said complexes with an evanescent wave resulting from a light wave which propagates through said optically transparent material;

e) detecting light scattered elastically by said light scattering particles of said complexes;

f) correlating elastically-scattered light to the presence of complexes on said sample contacting surface; and g) comparing the presence of complexes on the sample contacting surface with the presence of complexes on a sample contacting surface for a standard control, thereby detecting the analyte in the fluid sample.

Still another method is provided for detecting an analyte in a fluid sample, wherein said analyte is a ligand having an epitope for which a first ligand binding partner is specific and an epitope for which a second ligand binding partner is specific. This method comprises:

a) providing an optically transparent material having a refractive index greater than the refractive index of said fluid sample, said optically transparent material having a sample contacting surface to which a plurality of first ligand binding partners are immobilized;

b) further providing light scattering second ligand binding partners;

c) contacting said fluid sample and said light scattering second ligand binding partners with said sample contacting surface under conditions such that immobilized first ligand binding partner : analyte : light scattering second ligand binding partner complexes are formed;

d) illuminating said complexes;

e) detecting light scattered elastically by said light scattering second ligand binding partners of said complexes and which propagates through said optically transparent material from the sample contacting surface between the plane of the sample contacting surface and the total internal reflectance critical angle of the sample contacting surface;

f) correlating elastically-scattered light to the presence of complexes on said sample contacting surface; and g) comparing the presence of complexes on the sample contacting surface with the presence of complexes on a sample contacting surface for a standard control, thereby detecting the analyte in the fluid sample.

Within this application, "light scattering second ligand binding partners" means second ligand binding partners or particle labeled second ligand binding partners which cause incident light to be elastically scattered.

Still further is provided a method for detecting an analyte in a fluid sample wherein said analyte is a ligand having an epitope for which a first ligand binding partner is specific and an epitope for which a second ligand binding partner is specific. This method comprises:

a) providing an optically transparent material having a refractive index greater than the refractive index of said fluid sample, said optically transparent material having a sample contacting surface to which a plurality of first ligand binding partners are immobilized;

b) further providing light scattering second ligand binding partners;

c) contacting said fluid sample and said light scattering second ligand binding Partners with said sample contacting surface under conditions such that immobilized first ligand binding partner : analyte: light scattering second ligand binding Partner complexes are formed;

d) illuminating said complexes with an evanescent wave resulting from a light wave which propagates through said optically transparent material;

e) detecting light scattered elastically by said light scattering second ligand binding partners of said complexes and which propagates through said optically transparent material from the sample contacting surface between the plane of the sample contacting surface and the total internal reflectance critical angle of the sample contacting surface;

f) correlating elastically-scattered light to the presence of complexes on said sample contacting surface; and g) comparing the presence of complexes on the sample contacting surface with the presence of complexes on a sample contacting surface for a standard control, thereby detecting the analyte in the fluid sample.

In one embodiment of the present invention, the methods provided herein may be performed wherein the sample contacting surface is contacted with the fluid sample before being contacted with the light scattering particle-labeled second ligand binding partners or the light scattering second ligand binding partners. In another embodiment of the invention, the methods described herein may be performed wherein the sample contacting surface is contacted with the light scattering particle-labeled second ligand binding partners or the light scattering second ligand binding partners before being contacted with said fluid sample. Still further, the sample contacting surface may be simultaneously contacted with the fluid sample and the light scattering particle-labeled second ligand binding partners or the light scattering second ligand binding partner, e.g., the fluid sample may be mixed with the light scattering particle-labeled second ligand binding partners or the light scattering second ligand binding partners so as to form a mixture, and the mixture is contacted with the sample contacting surface.

Finally, in a preferred embodiment of the invention, the light scattering particle-labeled second ligand binding partners comprise second ligand binding partners which are labeled with colloidal gold particles.

First Series of Experiments

An apparatus embodying the principles of STIR was constructed utilizing an equilateral flint glass prism, Model 01-PES-007, obtained from Melles-Grist. The prism was mounted on a support with one side held horizontal. An antibody-coated cuvette in the form of a microtiter well, available from Dynatech under the trade name IMMULON TWO (styrene) was optically coupled to the horizontal prism surface with standard microscope oil. A five milliwatt helium neon laser (Hughes 3225-H-PC) was used to illuminate part of the cuvette's bottom surface at an angle 6° past the critical angle. Optionally, a cylindrical lens may be used to assist in focusing the laser light beam.

The critical angle was first determined by filling an uncoated cuvette, optically mounted on the prism, with a scattering aqueous medium comprising a mixture of colloidal gold sol produced pursuant to the method reported in Scanning Electron Microscopy Vol II, 9–31 (1981), Sear, Inc., AMF, O'Hare, Chicago, generating particle sizes of about 30 to 50 nm and serum. The prism was rotated along an axis transverse to the axis of the incident light until the laser beam path, visible inside the cuvette, optically disappeared indicating that substantially all of the incident light was being reflected at the cuvette-liquid interface, the internal reflectance phenomenon known to occur at the critical angle. This critical angle between a perpendicular line through the surface having the optically mounted cuvette and the laser beam was measured, the prism was reinstalled to provide a horizontal surface and the laser adjusted to illuminate the surface internally through the prism at an angle equal to 6° plus the critical angle. While a polarized laser was used with its polarization aligned with the electric field parallel to the plane of the styrene liquid interface, such is merely preferred but not necessary. Indeed virtually any collimated illumination source will serve. Similarly, while a prism was convenient, any optical coupling device for directing illumination toward the aqueous solid interface may be used such that total internal reflectance can be achieved by that interface.

A photodetector (Hamamatsu No. G1742 photodiode) was positioned at an angle above the critical angle but less than 90° at a position physically near the laser such that it would detect light scattered back toward the laser. In this position, minimal laser light is detected prior to the assay despite imperfections present at the interface.

Thus, placement of the photodetector above the critical angle is important in order to insure that light propagating through the solution, e.g., stray light or secondary light scatter induced by irrelevant sources, cannot reach the detector. As a related advantage, this greatly reduces the effect of the sample's color or turbidity and of bubbles present at the liquid interface.

The electrical signal from the photodetector was electrically coupled to a high gain current amplifier (Kiethly Electrometer 610-C) and the output recorded on a strip chart recorder or digitally recorded by a computer data acquisition system (HP controller 3497A with HP 9836 computer). Reaction rates were then graphically determined on the recorder chart or calculated conventionally employing the computer.

EXAMPLE 1 hCG Sandwich Assay

An anti-hCG antibody-coated cuvette (coated by standard physical adsorption) was positioned on the oil-coated prism with a laser internally reflecting off the center of the cuvette. 35 $\mu$ls of assay buffer (0.01 M phosphate buffered saline at a pH of 7.4 containing 1% bovine serum albumin, 1 M NaCl and 1.5 mg/ml mouse IgG) was added to the cuvette. 50 $\mu$ls of nonblocking, anti-hCG antibody coupled with colloidal gold (approximately 44 nm in size) was then added and mixed by pipette aspiration. 25 $\mu$ls of serum sample or serum-based standard (Gilford) was then added to the cuvette and mixed. The intensity of the scatter signal was recorded by a strip chart recorder and by a digital data acquisition system. The reaction rate was permitted to equilibrate for the first five minutes to permit the system to become linear and then measured kinetically during the next five minutes. Reaction rates (e.g. signal slopes) of unknown serum samples were compared to the reaction rates of standards in order to compute hCG concentrations. The results were as follows:

| Std. | Signal Slope (arbitrary units) |
| --- | --- |
| 0 mIU | 1.00 |
| 10 mIU | 7.43 |
| 25 mIU | 16.33 |
| 50 mIU | 32.03 |
| 100 mIU | 68.67 |
| 200 mIU | 130.97 |

EXAMPLE 2

Test For Antibody (Reverse hCG Sandwich Assay hCG antigen was coated onto Immulon cuvettes and positioned on the oil-coated prism as inn Example 1. 50 $\mu$ls of colloidal gold (approximately 45 nm) coated with hhCG was added to the cuvette along with 335 $\mu$ls of assay buffer as described in Example 1, and mixed. 25 $\mu$ls of mouse monoclonal anti-hCG containing standard (diluted in pH 8.3 HEPES/TRIS 0.225 M+0.5% BSA) was added and mixed. After a five-minute delay for equilibration, the rate was measured as in Example 1. As anti-hCG concentrations were increased up to 10 l$\mu$gs per ml, increasing rates of light scatter were observed with rates decreasing above this concentration giving the expected hook effect (e.g. insufficient labeled and immobilized antigen to accomodate all of the antibody present). The data was:

| Mouse IgG Conc. (ng) | Signal Slope (arbitrary units) |
| --- | --- |
| 0 ng | 8.02 |
| 10 ng | 10.27 |
| 100 ng | 12.35 |
| 1 $\mu$g | 75.84 |
| 10 $\mu$g | 91.39 |
| 100 $\mu$g | 37.00 |

EXAMPLE 3

Competition With Antigen-Coated Cuvette

Thyroxin (T4) was covalently coupled to BSA with approximately 20 T4 molecules per BSA molecule employing the following procedure. $T_4$-BSA conjugate was prepared from coupling BSA with $T_4MC$, L-Thyroxinyl-4-(N-maleimido-methyl)-cyclohexane-1-carbonate, through a nucleophilic addition at pH 9–0 by amino groups of BSA to the maleimido group of $T_4MC$. $T_4MC$ was derivatized from SMCC, succimimidyl-4-(N-maleimido-methyl)-cyclohexane-1-carboxylate (Pierce Chemical), with L-Thyroxine by amidation at neutral pH. $T_4$-BSA conjugate was absorbed to commercial, strip microtiter wells by incubating 0.1 mls of 0.17 mgs per ml of the conjugate in 0.01 M phosphate buffer adjusted to a pH of 7 at room temperature for 18 hours. The wells were washed three times with 0.25 M HEPES/TRIS buffer (containing 0.05% $NaN_3$, 0.15 M NaCl at a pH of 8.3). The wells were then incubated for 72 hours at room temperature with 0.2 mls of HEPES/TRIS buffer plus 1% BSA. The wells were then again washed three times with HEPES/TRIS buffer and stored with buffer at 4° C. until use.

Colloidal gold having an average diameter of 40 nm was coated with monoclonal anti-$T_4$ IgG by previously described methods. The strip well cuvettes were mounted on the prism as in Example 1 and 65 $\mu$ls of pH 7.4 PBS containing 0.02% $NaN_3$ and 2% bovine gammaglobulin was added to the cuvette followed by 10 $\mu$ls Of $T_4$ standard in the same buffer. 25 $\mu$ls of anti-$T_4$ antibody coated colloidal gold was then added to the cuvette and mixed. The reaction rate was measured after an equilibration period. As expected, increasing $T_4$ concentrations correlated with decreased signal rates from back scattered light signal as follows:

| $T_4$ ($\mu$g/dl) | Signal Slope (arbitrary units) |
|---|---|
| 0 | 51.1 |
| 2 | 41.9 |
| 4 | 25.3 |
| 8 | 9.08 |
| 12 | 6.51 |
| 24 | 2.96 |

EXAMPLE 4

Competition With Antigen-Coated Colloidal Gold

Immulon strip well cuvettes were coated with h0.1 mls of 5 $\mu$gs per ml of antigen-digoxin and 0.1 M $KPO_4$ at a pH 7.4 and stored at 4%C. until use. The wells were then washed three times with 0.01 m PBS at a pH 7.4. Colloidal gold particles having an average diameter of 40 nm were coated with h1 mg per ml of digoxin--BBSA conjugate (approximately 5 digoxins per BSA molecule) by the method set forth in an article by T. W. Smith, Biochemistry 9:331-337 (1970) and then diluted 1 to 4. 35 $\mu$ls of buffer 0.01 m PBS, 1.0 M NaCl, 1% BSA at pH 7.6) was added to the cuvette followed rapidly by the addition of 25 $\mu$ls of serum samples or serum base standard and 50 $\mu$ls of digoxin-coated colloidal gold suspension and mixed. The reaction rate was measured during the next five minutes and the results observed. Increasing digoxin concentrations resulted in reduced reaction rates as follows:

| Digoxin (ng/ml) | Signal Slope (arbitrary units, 2 runs) |
|---|---|
| 0 | 372, 296 |
| 0.25 | 127, 86 |
| 0.50 | 30, 29 |

EXAMPLE 5

Internalized Kinetic Calibrator

It will be recognized that there may be variation from well to well between assays as well as between liquid reagents added to the wells. These differences will result in variations in kinetic responses which could, without correction, lead to erroneous results. One preferred method of correction is to utilize an internalized kinetic calibrator. To do so, a low level control sample is added to the well at the beginning of every assay and the rate of reaction monitored for a short time prior to the addition of the sample to the same well. The control sample can thus be used to calibrate each individual well, e.g. measuring the well's sensitivity and using that information to correct the sample readings, thereby obviating differences in structural or reagent coating uniformity. Accordingly, homogeneous rate assays can be ideally performed by first adding a control sample and monitoring the level of detector output. As a related advantage, this procedure will eliminate the need to perform duplicate assays thereby saving in time and resource expenditures. Such a calibration procedure will also obviate the sample to sample variations in light scattering efficiency of the particles which is a strong function of the index of refraction of the individual sample. The following example of the procedure demonstrates the principles involved.

Molded polycarbonate cuvettes were adsorption coated with anti-hCG antibody. 150 $\mu$ls of assay buffer (from Example 1), 100 $\mu$ls of anti-hCG coated colloidal gold approximately 40 nms diameter) and 75 $\mu$ls of Gilford stripped serum based 10 mIU/ml calibrator were added to each cuvette and mixed. After 5 minutes incubation, the rate of increase of scattered light intensity (slope) was measured during the next 5 minutes. After recording this calibration slope, 75 $\mu$ls of Gilford serum based standard was added as sample, mixed and incubated 5 minutes before reading the scattered light slope during the next 5 minutes. The net calibrated slope of each cuvette was calculated by the equation:

Net calibrated slope = [slope of standard/slope of calibrator] − 0.8826

Where 0.8826 was the average slope of six zero hCG standards divided by their respective calibration slopes.

The CV (coefficient of variation) of six replicates of the following standards were calculated on the basis of the net calibrated slope and compared to the uncorrected slope of these standards. The data was as follows:

| mIU/ml of standard | CV of uncorrected | CV of Net Calibrated slope |
|---|---|---|
| 10 mIU/ml | 18.31% | 10.79% |
| 50 mIU/ml | 30.3% | 21.42% |
| 100 mIU/ml | 18.86% | 5.88% |
| 200 mIU/ml | 33.63% | 30.86% |

In all cases, it can be seen that greater accuracy and repeatability was obtained using the internal calibration method.

EXAMPLE 6

Competitive hCG Assay Using Latex Particles

Immulon strip wells were coated as stated in Example 1 above. 35 μls of assay buffer was added to each well. 25 μls of hCG dissolved in stripped serum (Gilford) was then added and mixed. After a 5 minute incubation, 50 μls of "Ortho Beta-hCG Slide Test for Pregnancy" hCG coated styrene latex (0.375 micron diameter) (Ortho Diagnostic Systems Inc.) was added and mixed. The reaction rate was permitted to equilibrate for 5 minutes while the slope of the scattered light signal was calculated during the next 5 minutes. The results were as follows:

| HCG Standard Concentration | Signal Slope (arbitrary units) | Average |
| --- | --- | --- |
| 223,875 mIU/ml | 3.61, 3.76, 6.04 | 4.47 |
| 22,387 | 8.96, 9.02, 9.25 | 9.08 |
| 2,238 | 118, 122, 144 | 128 |
| 223 | 158, 162, 187 | 169 |
| 22.3 | 148, 157, 196 | 167 |
| 2.2 | 138, 142, 161 | 147 |

EXAMPLE 7

Direct Red Cell Antigen Test using Red Cell Particle (approximately 8 micron diameter)

Polycarbonate cuvettes were coated by adsorption with anti-D (anti-Rh$_o$) for an RH factor test and with anti-A for an ABO blood group test. 0.5 ml of human whole blood was centrifuged, resuspended in 5 ml of phosphate buffered saline (PBS) pH 7.4, centrifuged and resuspended in 2 ml of PBS. 300 μls of this sample suspension was added to the coated cuvette and mixed. After a 2 minute incubation, the slope of the scattered light intensity was calculated over the next 8 or 18 minutes. The results were as follows:

Slope in anti-A Coated Cuvettes

| Sample Blood Type (RH Type) | Slope (Time) |
| --- | --- |
| Slope in anti-A Coated Cuvettes | |
| Red Cell Phenotype | |
| A− | 267 (8 min) |
| A+ | 240 (18 min) |
| B+ | −18.6 (.8 min) |
| O | 14.9 (18 min) |
| Slope in anti-D Coated Cuvettes | |
| A+ | 56.6 (18 min) |
| B+ | 10.2 (18 min) |
| O−D−(high positive RH)* | 32.3 (18 min) |
| A− | 4.3 (18 min) |
| O− | 4.5 (18 min) |

*rare blood type

It will be readily recognized by those skilled in the art that a certain amount of physical manipulation may be made to this system without substantially departing from either the spirit or the scope of the present invention. For example, the cuvettes and prism assembly may be one integral unit wherein the cuvette microtiter well is molded with a plastic prism forming part of the cuvette. Similarly, while an angle 6° above the critical angle has been found most preferred, it will be recognized that dependent upon the optical characteristics of the illumination source and the photodetector, certain variations above the critical angle may be more optimal and are too be deemed equivalent to the angle set forth herein. Further, measurements may take place on the side or bottom of the cuvette.

Further, while colloidal particles such as gold, latex and red blood cells have been described in the Examples, it should be recognized that particles and their particular size range are not to be deemed limitations but are merely exemplary of the wide range of possibilities. Indeed, the size of particles generally should be chosen with consideration given to the wavelength of the light in the liquid medium (in turn a function of the refractive index of the medium), the index of refraction of the particle should ideally be chosen with consideration given to the index of refractions of the aqueous medium and the solid so that the net effect is an optimum signal, most advantageously obtained when resonance of the system occurs. While predictability is exceedingly difficult given the current level of understanding of these complicated interactions, the actual optimization procedures are relatively simple and easily performed by those skilled in the art.

Second Set of Experiments

Figure 1:
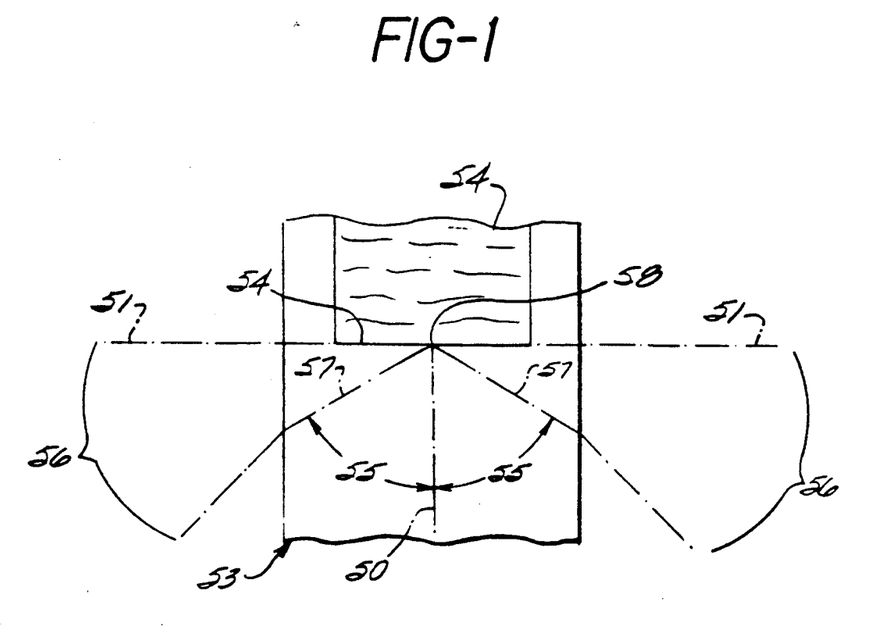
FIG. 1 depicts an optically transparent member 53 with refractive index $n_2$ having a fluid contacting surface 52 in contact with fluid 54 having a refractive index $n_1$ which is less than $n_2$. The total internal reflectance critical angle 55 measured from a line 50 perpendicular to the plane of the fluid contacting surface 51 is the minimum angle of illumination required to provide total internal reflectance at surface 52. This angle is defined by the equation $$\theta_c = \sin^{-1}\left(\frac{n_1}{n_2}\right)$$
Figure 2:
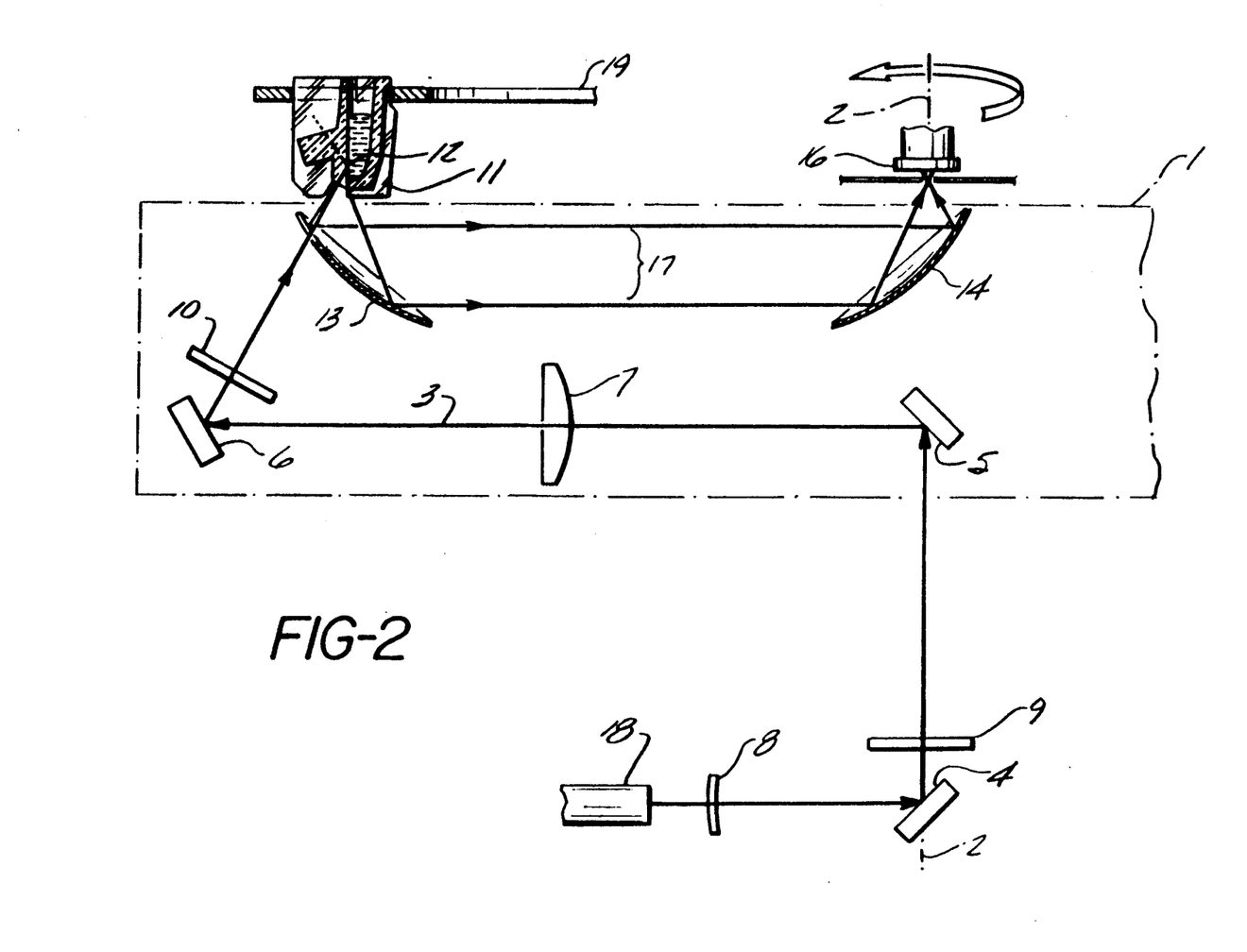
FIG. 2 is a simplified elevation view of the cuvette and the rotating optics mechanism used to illuminate and read it.

Referring to FIG. 2, a rectangular plate 1 is rotated at constant speed (by a motor, belt, and pulleys, not shown) in a horizontal plane about a vertical axis 2.

The following components are mounted on the rotating plate and travel with it: two front surface mirrors 5 and 6 (Melles Griot 02MFG000); a 150 mm focal length lens 7 (Melles Griot 01LPX237); a quarter-wave retardation plate 10 (Melles Griot 02WRM013-632.8); a paraboloidal reflector (axial cross-section 13) with a clearance notch to permit a laser beam to pass through; a second paraboloidal reflector 14 without a notch; and an aperture plate 15 (0.25 mm thick with a 2 mm hole centrally located about the rotational axis). The paraboloidal reflectors 13 and 14 have a focal length of 10.2 mm (Aero Research Associates 484-001). These are off axis segments of parabolic reflectors mounted with the optical axis of their parent parabolas coincident.

Beneath the rotating assembly is a polarized He-Ne laser 18 (5 mW, Melles Griot 05LHP151). The laser beam goes through a first quarter-wave retardation plate 8 (same as 10), is reflected off a front surface mirror 4 (same as 5 and 6), and passes through a second quarter-wave retardation plate 9 (same as 10). Each quarter-wave plate (8, 9 and 10) is mounted so that it can be rotated in a plane perpendicular to the laser beam for adjustment and can be locked in a position when correctly adjusted. When the laser beam emerges from plate 9, it is coincident with the axis of rotation 2 of the rotating optical assembly.

The three quarter-wave plates were used in this embodiment because the optical signal obtained from the scatter at cuvette surface 12 is sensitive to the polarization of the incident light. Thus in order to assure uniform results about the circle of cuvettes, the beam must be in the same polarization condition at all positions. To achieve this, a laser 18 producing a plane polarized beam was employed. This beam is given circular polarization by passing it through a properly oriented quarter-wave retardation Plate 8. A second retardation plate 9 is provided to permit fine tuning to compensate for imperfections in the characteristics of the first retardation plate. A third quarter-wave plate 10 on the rotating member is used to produce plane polarized light with the electric field parallel to the plane of cuvette surface 12.

The lens 7 is used to converge the laser beam 3 from 0.8 mm diameter as it enters the lens to 0.2 mm diameter at the total internal reflection surface 12. The small diameter facilitates multiple readings, which are averaged to improve instrument precision.

A plate 19 with receptacles for forty cuvettes is mounted above the rotating optics assembly. The receptacles are disposed in a circle whose center is the axis of rotation of the rotating optics assembly. One of the cuvettes is shown at 11. As the optical assembly rotates, it presents the laser beam and the receiving optics (the two paraboloidal reflectors) to each cuvette in turn. At each cuvette a plurality of readings is obtained as the assembly moves past the optical face of the cuvette.

Figure 3:
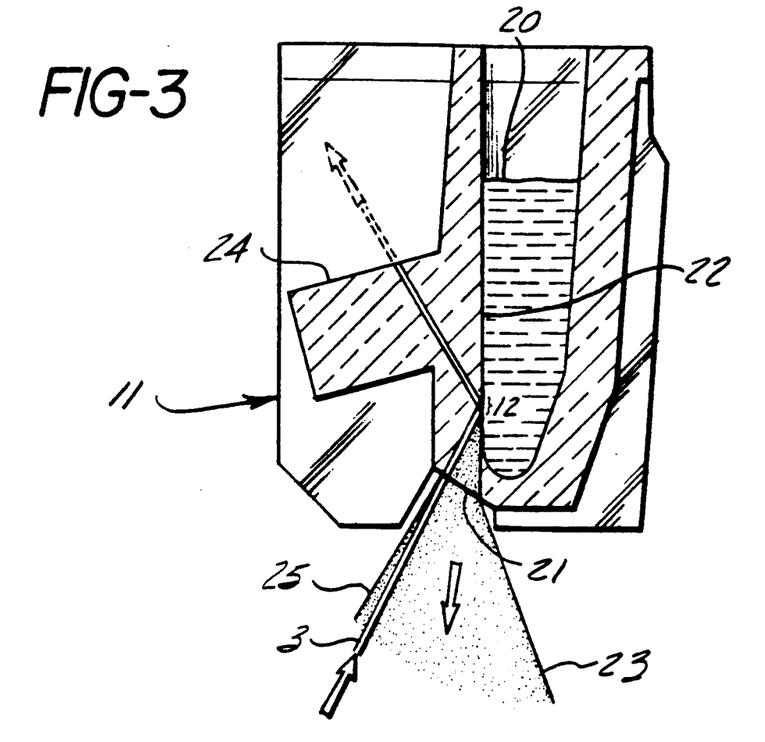
FIG. 3 is cross-section of a cuvette.

Referring to FIG. 3, the laser beam 3 enters face 21, travels through the transparent plastic material to surface 22, where it undergoes total internal reflection, and exits the cuvette at surface 24. The analyte solution is contained in the well 20. The signal-generating scatter occurs at 12.

The laser beam 3 is introduced into the entry face 21 slightly below the normal to the surface, so that any surface reflection of the laser beam is directed away from the receiving optics. The beam is refracted at the entry surface so that it impinges on the surface 22 at an angle from the normal to surface 22 greater than the critical angle. Thus it is totally internally reflected.

Figure 4:
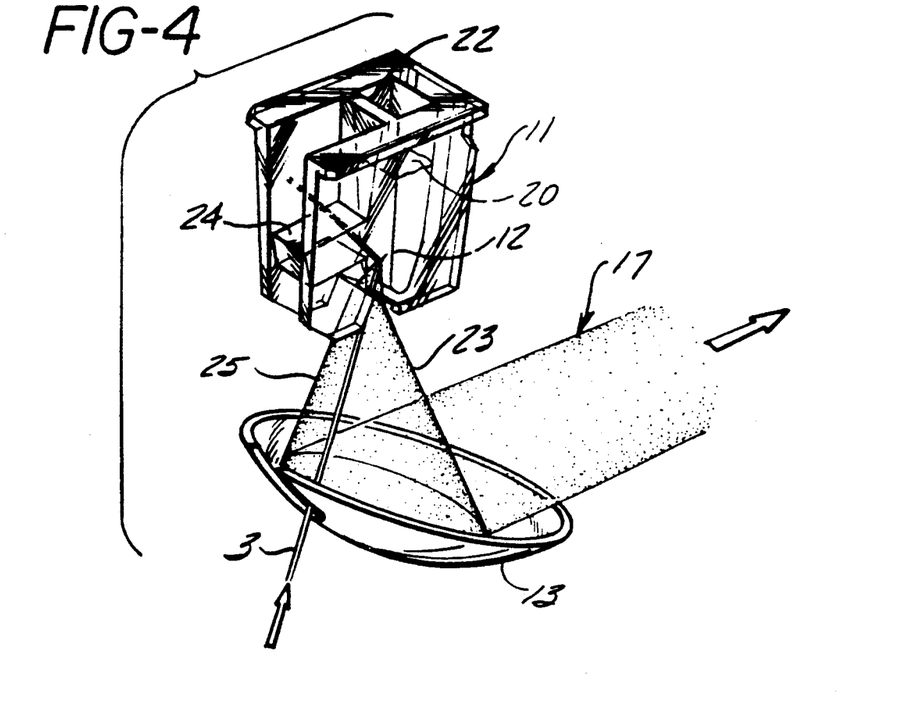
FIG. 4 is a perspective view of a cuvette and a paraboloidal reflector which is the first component of the receiving optics.

The sector (of a complete paraboloid) which is used at 13 (FIGS. 2 and 4) to collect the optical signal generated at the total internal reflection surface 12 is determined by the requirement to be at an angle greater than the critical angle and whereby only light scattered backward toward the light source is detected. Areas of the paraboloidal reflector 13 at lesser angles are masked with matte black pressure-sensitive paper tape. Thus only light originating from the total internal reflectance critical angle 25 to rays originating parallel to surface 12, shown as 23 in FIG. 2, are accepted.

The paraboloid is located so that the scatter source 12 is at its focus. Rays originating at the focus of a paraboloid are reflected parallel to its axis, so the signal light 23 to 25 (FIGS. 3 & 4) is transmitted as a beam 17 toward the second paraboloid 14. (See FIG. 4 for detail.) Rays Parallel to the axis of a paraboloid converge at the focus. The second paraboloid 14 concentrates the signal energy at its focus, where the aperture plate 15 is mounted. The aperture plate prevents stray light (not originating from the scatter source 12), which is not focused by the receiving optics, from reaching the photodetector 16. (Hamamatsu Corporation S1723-04).

An optical encoder (Sumtak Model LHF-050-2000, not shown) was attached to the rotating optical assembly. The output of this encoder was used to provide rotational information to an IBM PCAT and digital data acquisition system. As the laser/detector optics assembly 1 passes under each cuvette the digital data acquisition system/computer digitized and stored the average of approximately 100 signal readings of the amplified output of the detector 16, taken as the internal reflection surface 12 is scanned. Thus the average of approximately 100 readings obtained from each cuvette was stored with each rotation (one revolution approximately every 2 SeConds). The computer also stored a reading proportional to the laser output, from another detector, and readings of a low scattering region (laser impinging on black anodized aluminum cuvette holder ring 19) and high scattering region (teflon block mounted in place of cuvette). These readings were used to compensate for variations in laser intensity and for detector drift. When the computer monitored the cuvettes for 10 minutes it generated a 5th order least squares approximation equation to the scatter signal vs. time data for each cuvette, subtracted the signal at time =0 seconds from the curve and integrated this equation vs. time for each cuvette. This integral was then correlated with analyte concentration.

EXAMPLE 1

Hepatitis Virus Surface Antigen Test

Polycarbonate cuvettes, as depicted in FIG. 3, were coated with mouse monclonal anti-hepatitis surface antigen antibodies by incubating 200 microliters of a 100 microgram per ml solution of antibody in 0.01 M phosphate buffered saline, pH 7.4, overnight at room temperature followed by three aspirate fill steps with 300 microliters of 0.05 M Hepes/Tris, pH 8.3 buffer. The cuvettes were then overcoated with 300 microliters of 0.05 M Hepes/Tris, pH 8.3, buffer containing 1% bovine serum albumin for 60 minutes at room temperature, washed twice with 300 microliters of overcoating solution, incubated 15 minutes at room temperature with 300 microliters of 3% trehalose in 0.05 M Hepes/Tris, pH 8.3 buffer, aspirated, dried in room air and stored at room temperature in a desicator below 20% relative humidity. The cuvettes were then mounted in an instrument similar to that depicted in FIG. 2 with the modification that the cuvette was rotated 180° about the illuminated surface 12 and the laser entered the cuvette while propagating away from the axis of rotation, still following the path inside the cuvette depicted in FIG. 3.

Seventy-two microliters of standard, prepared by adding the appropriate amount of hepatitis surface antigen from (Merck) to a negative serum pool, was dispensed into cuvettes by an automated pipetter and allowed to incubate in the enclosed 37° C. instrument for five minutes. The pipetter then dispensed 54 microliters of buffer (containing 2.0 M potassium chloride, 2% bovine serum albumin, 50 micrograms per ml of normal mouse IgG and 0.051% sodium azide dissolved in 0.05 M sodium barbitol buffer at pH 8.5) and 180 microliters of 105 nm diameter 0.1% monoclonal anti-hepatitis surface antigen coated gold colloid suspension (in ten mM Hepes buffer, pH 7.0, containing 0.05% sodium azide, 300 mM mannitol, and 0.5% bovine serum albumin) at a rate sufficient to mix the fluids in the cuvette. The light scattered by each cuvette was then recorded for the next ten minutes. The time integral of the fifth order linear regression curve fit of the light scatter vs. time data was reported for each cuvette. The average of the signal from five of the six zero standards (one was 14 standard deviations from mean of the other five) and the average of the duplicate standards correlated proportionately with the hepatitis surface antigen present, as can be seen from the following data :

| HEPATITIS SURFACE ANTIGEN CONCENTRATION | MEAN SIGNAL |
| --- | --- |
| 0 | 1.7358 |
| 0.1 ng/ml | 2.2376 |
| 0.2 ng/ml | 2.9421 |
| 0.4 ng/ml | 3.99235 |
| 0.6 ng/ml | 5.0442 |

-continued

| HEPATITIS SURFACE ANTIGEN CONCENTRATION | MEAN SIGNAL |
|---|---|
| 0.8 ng/ml | 6.72185 |
| 1.0 ng/ml | 7.0187 |
| 1.5 ng/ml | 9.31175 |
| 2.0 ng/ml | 10.7365 |
| 2.5 ng/ml | 14.0444 |
| 5.0 ng/ml | 24.9279 |
| 10.0 ng/ml | 47.4585 |

EXAMPLE 2

Anti-Hepatitis Core Antigen Human Antibody Test

Polycarbonate cuvettes, as depicted in FIG. 3 were coated as in Example 1 (Second Set of Experiments), with recombinant hepatitis core antigen using a 5 microgram per ml coating solution. The cuvettes were then dried, stored and mounted in the instrument (FIG. 2), which was enclosed and equipped with 37° air circulation. Seventy-two microliters of the appropriate sample or control were added to separate cuvettes by an automated pipettor and allowed to incubate for 5 minutes, after which time 54 microliters of assay buffer (consisting of 1% bovine serum albumin and 1 M NaCl dissolved in pH 7.4 phosphate buffered saline) and 180 microliters of a 0.1% suspension of 105 nanometer diameter mouse monoclonal anti-human IgG coated colloidal gold suspension was dispensed with sufficient velocity to mix the contents of the cuvette. The light scattered by the cuvette was then recorded for the next 10 minutes. The time integral of the fifth order linear regression curve fit of the scattered light vs time data was reported for each cuvette as signal. The mean signal of replicates of each serum sample correlated with the presence of anti-hepatitis core antigen employing a cutoff of 3 standard deviations above the mean of the negative control, as shown in the following data:

| SAMPLE TYPE | # OF REPLICATES | MEAN | TEST OUTCOME |
|---|---|---|---|
| Negative control | 4 | 0.9524 | S.D. = 0.51 |
| Positive control | 4 | 60.2099 | S.D. = 6.5 |
| Negative sample 1 | 2 | 2.1671 | — |
| Positive sample 1 | 2 | 10.483 | + |
| Positive sample 2 | 2 | 41.058 | + |
| Positive sample 3 | 2 | 33.494 | + |
| Positive sample 4 | 2 | 2.6043 | + |
| Positive sample 5 | 2 | 74.2235 | + |

Third Set of Experiments

EXAMPLE 1

Figure 5:
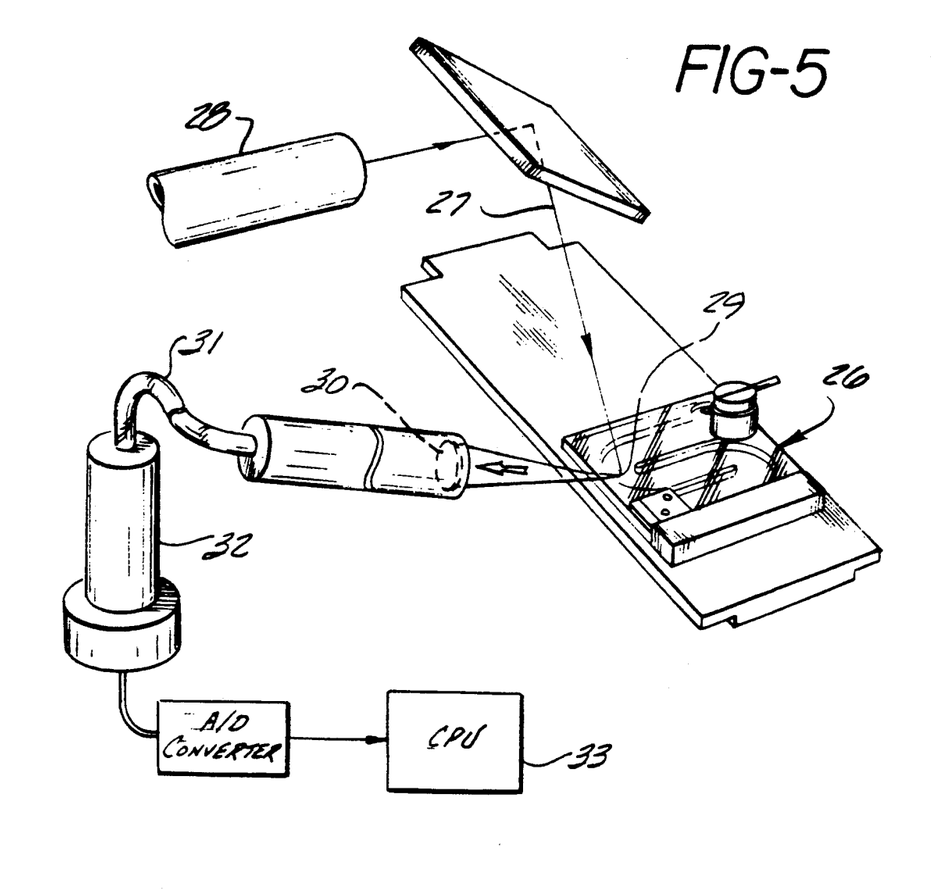
FIG. 5 depicts an apparatus with laser illumination above critical angle.
Figure 6:
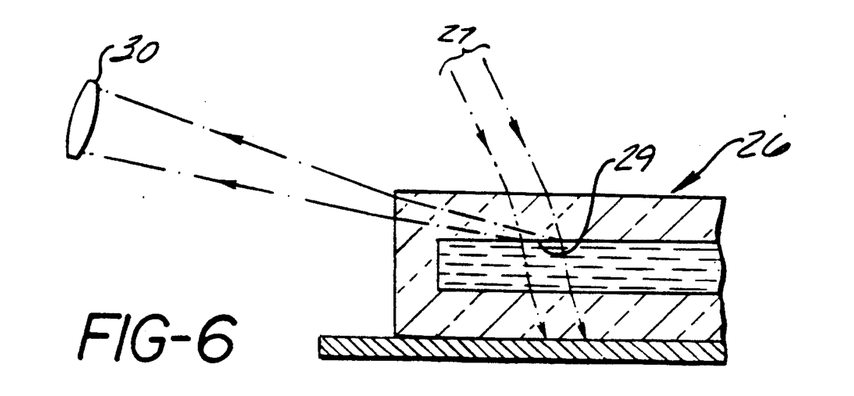
FIG. 6 depicts illumination and detection light paths used when illumination is above the critical angle.

Test for Digoxin in Whole Blood Sample Using Scatter by Colloidal Gold of Light Incident at Non-Total Internal Reflectance Angles The apparatus used in this Example is shown in FIGS. 5 and 6. Tests were performed on an acrylic cartridge 26 (Arden Medical Systems) with a channel for the sample to flow through. The surface of the channel was coated with polyclonal goat-anti-digoxin antibody (Atlantic Antibody) by standard passive adsorption methods Light 27 from a He-Ne laser 28 illuminated a portion of the coated surface 29 at an angle almost normal to the surface. At this angle of illumination, the light propagated into aqueous samples rather than producing an evanescent wave in the sample. Light scattered from the coated surface 29 was collected by a lens 30 and focussed onto an optical fiber 31, which guided the light to a photomultiplier tube 32 (PMT). The output voltage of the PMT was digitized and recorded by a computer 33. The detection system (lens and fiber) was carefully positioned and oriented so as to collect only light scattered from the coated surface 29 which propagated through the acrylic at angles between the plane of the surface and the critical angle.

Colloidal gold was prepared as described above (diameter approximately 40 nm.) and was coated with digoxin/bovine IgG. Whole blood was spiked with various amounts of digoxin Samples containing equal mixtures of spiked whole blood and digoxin-colloidal gold were pipetted into the cartridge and the resulting light scatter was monitored over time.

Figure 7:
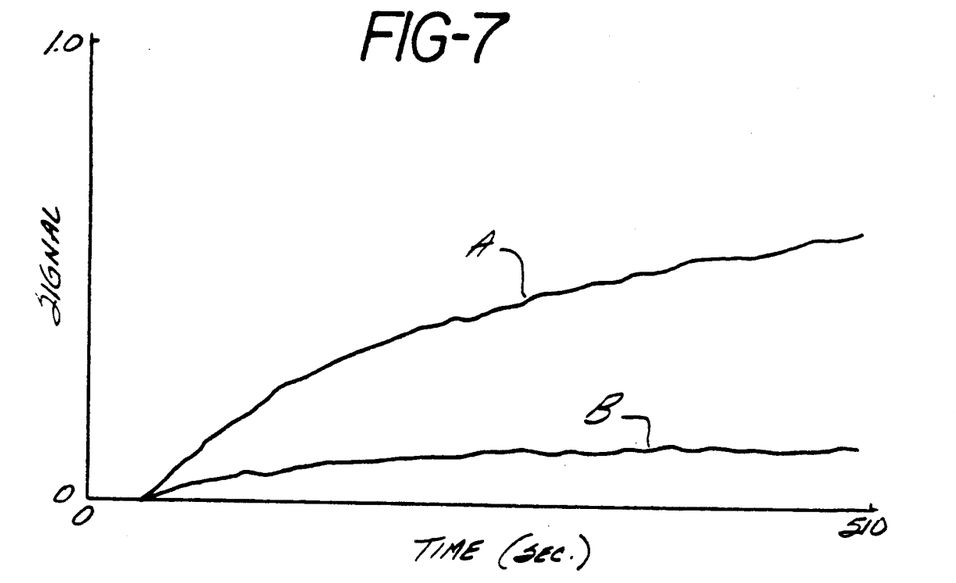
FIG. 7 shows data obtained with the apparatus of FIG. 5.

FIG. 7 shows typical results. In curve A, the sample contained no free digoxin, and the light scatter signal increased continuously during the seven minutes shown, as the digoxin-colloidal gold bound to the surface. In curve B, the whole blood sample contained approximately 4.5 µg/ml of digoxin which competes with the digoxin-colloidal gold for sites on the coated surface, and as a result the scatter signal leveled off after a few minutes. (The curves have been offset so that they start at the same level for comparison.)

In this example, the sample was below the coated surface. When the sample is above the coated surface, the settling of red blood cells causes large spurious scatter signals. For whole blood assays, applicants have found that it is preferable to orient the coated surface such that gravity pulls the red blood cells away from the surface, or at least does not pull them towards the surface.

EXAMPLE 2

Observation of Immunological Binding of Colloidal Gold with LED as Light Source

Figure 8:
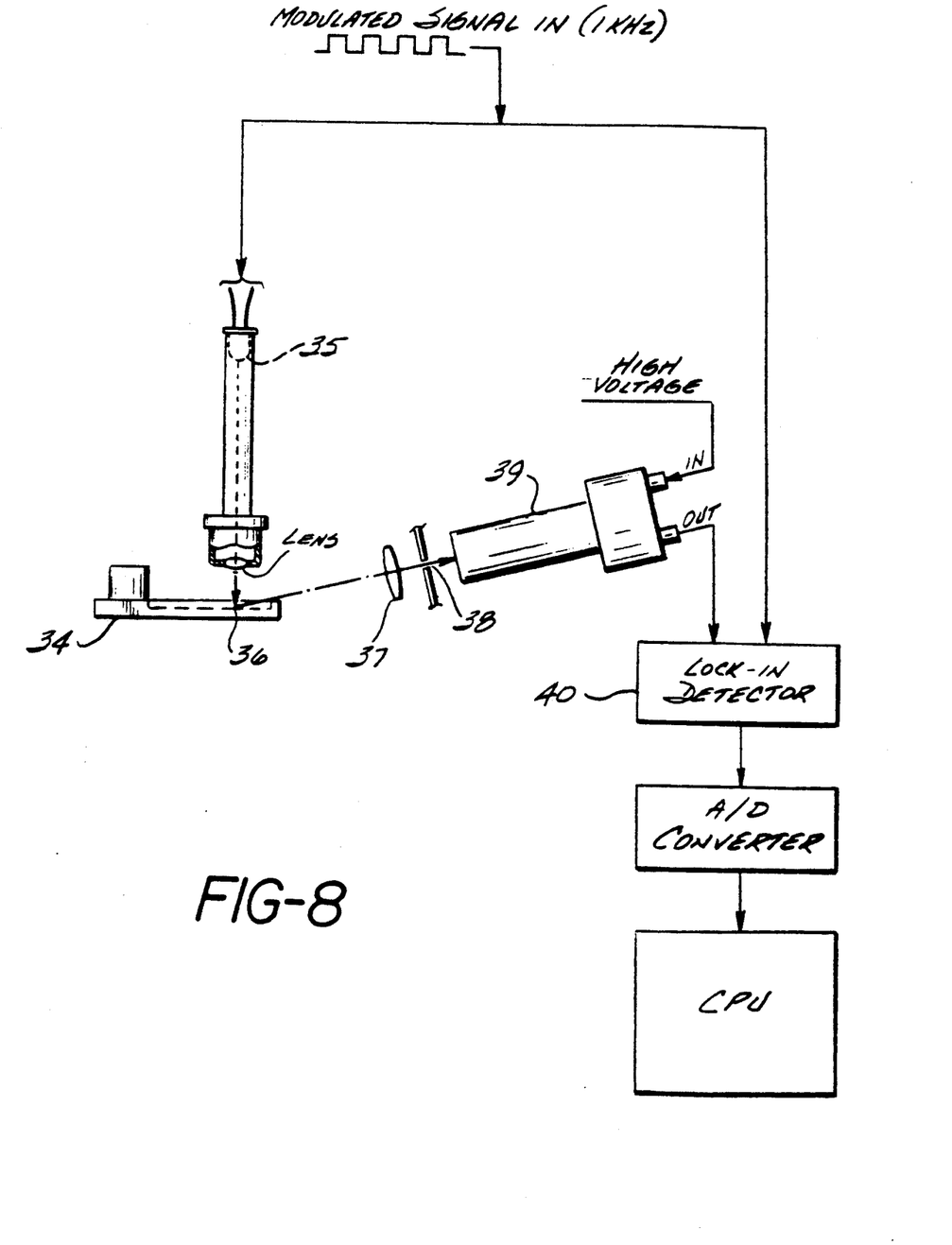
FIG. 8 depicts an apparatus with light emitting diode illumination above the critical angle.

The apparatus used in this Example is shown in FIG. 8. The tests were performed on the same acrylic cartridge 34 as in Example 1 (Third Set of Experiments). The light source 35 was a red light-emitting diode (LED, Stanley ER-300, 300 millicandela, 660 nm. peak wavelength, 30 nm. half-width). Light from the LED was focussed on the coated surface 36 by a 10X microscope objective. Scatter from the surface was focussed by a lens 37 on an aperture 38 and then to a PMT 39 with the same optical alignment conditions described in Example 1 (Third Set of Experiments). The LED output was electronically modulated at 1 KHz and the PMT output was demodulated at the same frequency by a lock-in amplifier 40 (PAR 128A) to improve signal-to-noise performance of the apparatus.

Figure 9:
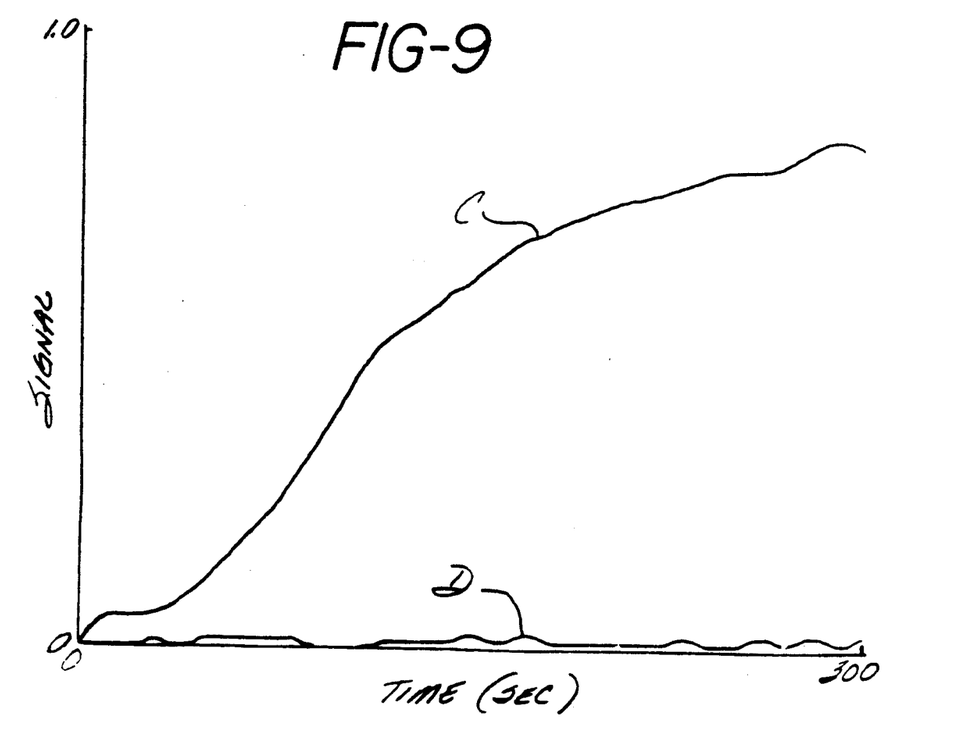
FIG. 9 shows data obtained with the apparatus of FIG. 8.

The reagent used in this Example was 40 nm. colloidal gold coated with goat-anti-mouse antibodies (Janssen "AuroProbe"). This reagent was pipetted into cartridges coated with Mouse IgG or Bovine Serum Albumin (BSA). FIG. 9 shows typical results. Curve C shows a substantial increase in scatter signal as the GAM-gold binds to a cartridge coated with MIgG. Curve D shows little response when the cartridge was coated with BSA.

What is claimed is:

1. An apparatus for detecting the presence of an analyte of interest inn a sample which comprises:
   a light source;

housing means for receiving an optically transparent member having a sample contacting surface, said member in said housing means being disposed such that the sample contacting surface is illuminated with light emitted from said light source; and photodetection means which excludes the detection of light which propagates in a geometric optical path from the light source, said photodetection means being capable of detecting elastically-scattered light which propagates through the optically transparent member from the illuminated sample contacting surface between the plane of the sample contacting surface and the total internal reflectance critical angle of the sample contacting surface; said photodetection means comprising a rotatable optical means comprising a first reflecting means and a second reflecting means whose optical axis is nearly coincident with the optical axis of said first reflecting means, whereby said elastically-scattered light is concentrated to facilitate detection thereof, said first reflecting means located to receive said elastically-scattered light and said second reflecting means located to receive light reflected from said first reflecting means.

2. An apparatus for detecting the presence of an analyte of interest in a sample which comprises:

a light source;

housing means for receiving an optically transparent member having a sample contacting surface, said member in said housing means being disposed such that the sample contacting surface is illuminated with light emitted from said light source which propagates through the optically transparent member at angles between the plane of the sample contacting surface and the critical angle for total internal reflectance; and photodetection means which excludes the detection of light which propagates in a geometric optical path from the light source, said photodetection means being capable of detecting elastically--scattered light which propagates through the optically transparent member from the illuminates sample contacting surface between the plane of the sample contacting surface and the total internal reflectance critical angle; said photodetection means comprising a rotatable optical means comprising a first reflecting means and a second reflecting means whose optical axis is nearly coincident with the optical axis of said first reflecting means, whereby said elastically-scattered light is concentrated to facilitate detection thereof, said first reflecting means located to receive said elastically-scattered light and said second reflecting means located to receive light reflected from said first reflecting means.

3. The apparatus of claim 2 wherein said optically transparent member comprises a molded polymeric cuvette.

4. The apparatus of claim 3 wherein said sample contacting surface of said optically transparent member comprises one surface of a sample receiving cavity.

5. The apparatus of claim 3 wherein the first surface illuminated by light source is aligned to specularly reflected said light so that it is not detected by said photodetection means.

6. The apparatus of claim 2 wherein said first and second reflecting means are paraboloidal reflectors.

7. The apparatus of claim 6 wherein said paraboloidal reflectors are off-axis segments of said paraboloidal reflectors.

8. The apparatus of claim 2 further comprising:
a non-rotating first means to convert the light emitted from said light source from plane polarized light into circularly polarized light;
a second means located on said rotatable optical means to reconvert the polarized light received from said first means to plane polarized light.

9. The apparatus of claim 8 wherein said means to convert said light comprise one-quarter wave retardation plates.

10. The apparatus of claim 8 wherein:
said housing means is adapted to receive a plurality of said optically transparent members arranged in a circle above said rotatable optical means, which circle is centered on the rotational axis of said rotatable optical means,
each of said optically transparent members comprising a molded polymeric cuvette having a sample contacting surface which can be illuminated by said light source and aligned to specularly reflect said light so that it is not detected by said photodetection means,
said rotatable optical means adapted to present polarized light to each cuvette in turn, and
said photodetection means further comprising an optical encoder coupled to the rotatable optical means.

11. The apparatus of claim 2 further comprising:
a non-rotating first means to convert the light emitted from said light source from plane polarized light into circulatory polarized light;
a second means located on said rotatable optical means to reconvert the polarized light received from said first means to plane polarized light; and
a third means to optimize said polarization achieved by said first and second means.

12. The apparatus of claim 11 wherein said non-rotating means to convert said light comprise one-quarter wave retardation plates.

13. The apparatus of claim 2 further comprising an aperture whereby other than said elastically-scattered light is substantially excluded.

14. The apparatus of claim 13 wherein said aperture comprises a rotating aperture which rotates with said rotatable optical means.

15. The apparatus of claim 2 further comprising an optical encoder coupled to the rotatable optical means.

16. A method for detecting the presence of a light scattering molecule on the surface of an optically transparent material which comprises illuminating said light scattering molecule from light through rotating optical reflectors detecting light scattered elastically by said light scattering molecule which propagates through said optically transparent material between the plane of the surface of the optically transparent material on which the light scattering molecule is located and the total internal reflectance critical angle of the surface on which the light scattering molecule is located, and correlating detected, elastically-scattered light to the presence of the light scattering molecule on the surface of the optically transparent material.

17. A method for detecting the presence of a light scattering molecule on the surface of an optically transparent material which comprises illuminating said light scattering molecule with an evanescent wave resulting from a light wave which propagates through said optically transparent material from light through rotating optical reflectors, detecting light scattered elastically by said light scattering molecule which propagates through said optically transparent material between the plane of the surface of the optically transparent material on which the light scattering molecule is located and the total internal reflectance critical angle of the surface on which the light scattering molecule is located, and correlating detected, elastically-scattered light to the presence of the light scattering molecule on the surface of the optically transparent material.

18. The method of claim 17 wherein the detecting step further comprises:
obtaining a plurality of readings of said elastically-scattered light by moving said light source across said sample contacting surface and recording said readings at discrete locations identified by means of an encoder.

19. The method of claim 18 wherein the step of obtaining a plurality of readings is performed once per revolution of said rotating optical reflectors.

* * * * *